United States Patent [19]

Bliznjuk et al.

[11] 4,212,862

[45] Jul. 15, 1980

[54] O,O-DIARYL-1-ACYLOXY-2,2,2-TRICHLOROETHYLPHOSPHONATES AND FUNGICIDES BASED THEREON

[76] Inventors:
Nikolai K. Bliznjuk, Molodogvardeiskaya ulitsa, 36, korpus 6, kv. 62, Moscow; Ljudmila D. Protasova, Odintsovsky raion, p/o B.Vyazemy, 7, kv. 37, Moskovskaya oblast; Tatyana A. Klimova, Odintsovsky raion, Djutkovo, 5, kv. 65, Moskovskaya oblast; Rimma S. Klopkova, Odintsovsky raion, p/o B.Vyazemy, 16, kv. 20, Moskovskaya oblast; Vasily D. Tkachev, Odintsovsky raion, p/o B.Vyazemy, 8, kv. 4, Moskovskaya oblast; Evgeny F. Granin, ulitsa Oktyabrskaya, 91, kv. 42, Krasnodar; Mikhail P. Umnov, Kutuzovsky prospekt, 5, kv. 334, Moscow; Rev V. Streltsov, Odintsovsky raion, p/o B.Vyazemy, 3, kv. 54; Oleg V. Klimov, Odintsovsky raion, p/o B.Vyazemy, 7, kv. 37, both of Moskovskaya oblast; Sergei G. Zhemchuzhin, ulitsa Dnepropetrovskaya, 23, kv. 66; Rudolf P. Bulankin, ulitsa Menzhinskogo, 28, korpus 3, kv. 196, both of Moscow; Valery P. Chernyshev, Schelkovo, ulitsa Kosmodemyanskoi, 15, korpus 1, kv. 35, Moskovskaya oblast; Fialka G. Safina, ulitsa Komarova, 13-b, kv. 1, Moskovskaya oblast; Alla I. Terekhova, Schelkovo, ulitsa Sirenevaya, 6/1, kv. 80, Moskovskaya oblast; Eleonora I. Zaikina, Schelkovo, ulitsa Sirenevaya, 6/1, kv. 23, Moskovskaya oblast; Alexandr N. Bliznjuk, Molodogvardeiskaya ulitsa, 36, korpus 6, kv. 62; Valentina A. Rusakova, ulitsa Valtera Ulbrikhta, 20, kv. 20, both of Moscow; Julia N. Ivanchenko, Odintsovsky raion, p/o B.Vyazemy, 8, kv. 12, Moskovskaya oblast; Natalya S. Svistunova, Odintsovsky raion, p/o B.Vyazemy, 8, kv. 16, Moskovskya oblast; Viktor K. Promonenkov, Veshnyakovskaya ulitsa, 31, kv. 307, Moscow, all of U.S.S.R.; Lev N. Chudov, deceased, late of Moskovskaya oblast, U.S.S.R.; by Ljudmila A. Chudova, administrator, poselok Zagoryanskaya, ulitsa Dostoevskogo, 13; by Vladimir L. Chudov, administrator, Schelkovo, ulitsa Pustovskaya, 4, kv. 32, both of Moskovskaya oblast, U.S.S.R.

[21] Appl. No.: 953,451

[22] Filed: Oct. 23, 1978

[51] Int. Cl.[2] .......................... A01N 9/36; C07F 9/40

[52] U.S. Cl. .................................... 424/212; 260/952

[58] Field of Search ........................ 260/952; 424/212

[56] References Cited

U.S. PATENT DOCUMENTS 2,956,920 10/1960 Perkow ............................ 260/952

FOREIGN PATENT DOCUMENTS 463676 3/1975 U.S.S.R. ................................ 260/952

*Primary Examiner*—Anton H. Sutto

*Attorney, Agent, or Firm*—Lackenbach, Lilling & Siegel

[57] ABSTRACT

The present invention relates to novel O,O-diaryl-1-acyloxy-2,2,2-trichloroethylphosphonates of the formula:

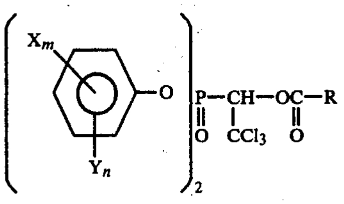

wherein R is a $C_1$-$C_8$ alkyl, phenyl; X and Y are the same or different and are each selected from hydrogen, a $C_1$-$C_8$-alkyl, phenyl, a halogen, or X and Y together form a fragment of a benzene ring, m and n=1−2.

The compounds possess a fungicidal activity and are incorporated in fungicidal compositions as active components.

The fungicides according to the present invention are effective not only for prophylactic use, but for the treatment of already infected plants. The fungicidal compositions are also efficient in various agroclimatic conditions and provide a substantially longer period of fungicidal effect as compared to conventional fungicides.

7 Claims, No Drawings

O,O-DIARYL-1-ACYLOXY-2,2,2-TRICHLOROETHYLPHOSPHONATES AND FUNGICIDES BASED THEREON

FIELD OF THE INVENTION

The present invention relates to chemical agents intended for treating diseases of farm crops and, more particularly, to novel organo-phosphorous compounds processing fungicidal activity.

BACKGROUND OF THE INVENTION

Organo-phosphorus fungicides are now extensively employed mainly for treating rice diseases caused by fungi Piricularia oryzae and Pellicularia sasaki (cf. A. F. Granov, N. N. Melnikov "Uspekhi Khimii", 1973, 42, 9, 1681).

Fungitoxical agents are found among different types of organo-phosphorus compounds including derivatives of phosphoric and phosphonic acids, phosphines and phosphonium salts, acids of tetracoordination phosphorus and salts thereof, esters of acids of tetracoordination phosphorus, and amides of phosphorus acids.

As a fungicidal thereapeutic compound for treating dermatomycoses known in the art is O,O-dimethyl-1-acetoxy-2,2,2-trichloroethylphosphonate (chloracetophos)—the closest analogue of the novel compounds according to the present invention cf. USSR Inventor's Certificate No. 280768, Bulletin of inventions, 1970, No. 28, p. 93).

Currently known organo-phosphorus fungicides are slightly effective against plant diseases, in particular in killing rust fungi causing most dangerous diseases of cereal and other crops.

For successful control of rust diseases of cereal crops being cultivated in vast areas, highly-effective fungicides are needed that are suitable for efficient application methods, e.g. for the ultra-small volume spraying (USVS) method.

A high activity in respect of rust diseases of cereal crops is revealed by dithiocarbamic acid derivatives, in particular by zinc ethylenebisdithiocarbamate (zineb). These fungicides, however, ar not suitable for application by the USVS method. Besides, these products are not stable upon storage and are harmful to human beings as well as the environment (1. Choinka A., Mosinski S. Pr. Inst.przem. organ., 1971, 3, 269; 2. Ivanova-Chemishanskaja "Gigiena i Sanitaria" 1971, No. 11, 95; 3. E. A. Antonovich et al. "Gigiena i Sanitaria", 1972, No. 9, 25). An essential disadvantage of dithiocarbamate fungicides resides in their limited application, i.e. they are effective only for the purpose of prophylaxis (prior to appearance of visualized symptoms of the disease). For this reason, their application may be effective only upon availability of trustworthy forecasts of disease development.

The above-mentioned disadvantages of dithiocarbamate fungicides gave rise to investigations aiming at finding appropriate substitutes therefor (cf. Gibney L., Chem. and Eng. News, 1975, 53, No. 23, 15).

A high activity against rust diseases is inherent in salts of nickel or mixtures thereof with ethylenebisdithiocarbamic acid derivatives (cf. Jones R. J., E.Afric.Agric. and Forest J., 1961, 26, No. 4, 210; Hardison J. R., Phytopathology, 1963, 53, No. 2, 209). However, due to a detrimental effect of said compounds on human organisms and environments, the use of nickel-containing fungicides has been prohibited (cf. J. Horsefall, Presentation to VIII Congress on Plant Protection, Moscow, 1975).

Ammonium salts of sulphanilic acid such as anilate have been suggested for killing rust fungi of cereal crops and other plants (cf. USSR Inventor's Certificate No. 178236, 1964; Bulletin of inventions, 1966, No. 2, 138). These compounds, however, are phytotoxic and of low-efficiency.

Certain modern system fungicides have proven to be efficient in killing rust fungi, e.g. 1,4-dioxide-2,3-dihydro-6-methyl-5-phenylcarbamoyl-1,4-oxathiine (hydroxycarboxine, plantwax), cf. "Systemic Fungicides", "MIR" Publishing House, 1975, p. 209. However, the use of these fungicides for treating rust diseases of cereal crops is in most cases economically inefficient due to the high cost of the compounds.

OBJECT OF THE INVENTION

It is an object of the present invention to provide novel, readily available, inexpensive organo-phosphorus fungicides that are not harmful to human beings or the environment and which possess a wide spectrum of activity, particularly in the effective treatment of rust diseases of cereal crops and suitable for application by different methods including the USVS method.

SUMMARY OF THE INVENTION

This object is accomplished by the provision of novel organo-phosphoric compounds of O,O-diaryl-1-acyloxy-2,2,2-trichloroethylphosphonates of the formula:

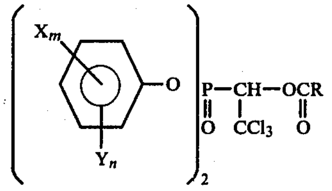

wherein R is a $C_1$-$C_8$-alkyl or phenyl, X and Y are the same or different and each represent hydrogen, a $C_1$-$C_8$-alkyl, phenyl, a halogen, or X and Y together form a fragment of a benzene ring; m and n=1 to 2.

It has been found that said compounds possess fungicidal activity and may successfully be used as fungicides.

The fungicidal composition according to the present invention contains, as the active principle, said O,O-diaryl-1-acyloxy-2,2,2-trichloroethylphosphonate and a carrier therefor.

DETAILED DESCRIPTION OF THE INVENTION

The compounds according to the present invention are prepared by acylation of corresponding O,O-diaryl-1-hydroxy-2,2,2-trichloroethylphosphonates by carboxylic acids or anhydrides thereof according to the scheme:

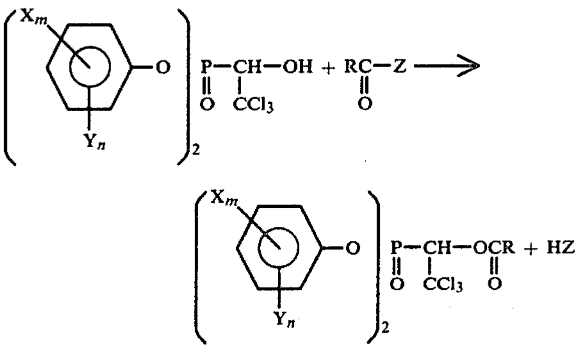

wherein Z is OH or

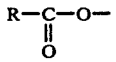

R, X, Y, m, n are as identified above.

The starting O,O-diaryl-1-hydroxy-2,2,2-trichloroethylphosphonates may be prepared by several methods:

by reacting a triarylphosphite, phosphorus trichloride and chloral hydrate (or chloral and water):

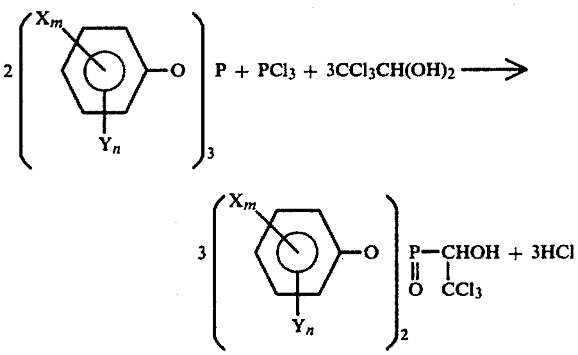

by reacting a mixture of the reaction products of two mols of a corresponding phenol (or a mixture of phenols) and one mole of phosphorus trichloride with chloral hydrate (or chloral and water):

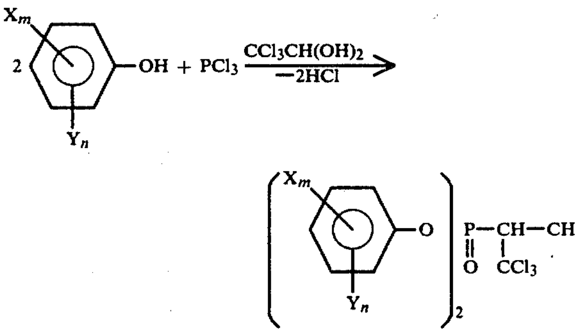

reaction in the system: a corresponding phenol, phosphorus trichloride and chloral hydrate:

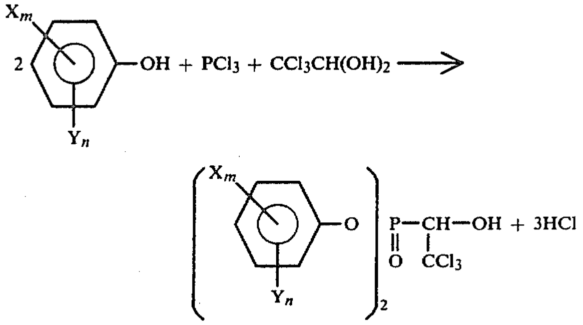

wherein X, Y, m, n are as identified above.

The above-mentioned reactions may be carried out in an inert organic solvent or therewithout. The resulting, O,O-diaryl-1-hydroxy-2,2,2-trichloroethylphosphonates (or mixtures thereof) may be used for acylation without separation, since they are produced substantially pure.

For the synthesis of O,O-diaryl-1-acetoxy-2,2,2-trichloroethylphosphonates it is advisable to use acetic anhydride as the acylation agent and to carry out the reaction in the absence of a solvent without separation of an intermediate O,O-diaryl-1-hydroxy-2,2,2-trichloroethylphosphonate. The embodiment is characterized by a simple technology, availability of semi-products (phosphorus trichloride, phenol, acetic anhydride and chloral hydrate or chloral and water), a high yield of the desired compounds, absence of waste waters and production wastes.

The compounds according to the present invention comprise 10-melting crystalline products or viscous oils stable upon storage, soluble in common organic solvents including aliphatic and aromatic hydrocarbons, chlorinated hydrocarbons, alcohols, ketones. This makes it possible to prepare, on the basis of said compounds, preparative forms suitable for the application by the USVS method (ultra-small-volume spraying) and build-up necessary stock of the compositions.

As to their fungicidal activity with respect to rust diseases of cereal crops the compounds according to the present invention, in particular their most trivial representative O,O-diphenyl-1-acetoxy-2,2,2-trichloroethylphosphonate, are superior over the prior art anti-rust fungicidal compositions including zineb and hydroxycarboxine. The fungicidal preparation containing, as the active principle, O,O-diphenyl-1-acetoxy-2,2,2-trichloroethylphosphonate will be referred to hereinafter as "APHOS". Using aphos in both high-volume spraying and in the treatment of plants by the USVS method at a rate of from 5 to 8 l/ha, it is possible to substantially completely protect cereal crops from rust even at a high level of infection and obtain an increase of the grain yield of up to 24 c/ha.

An essential advantage of the fungicides according to the present invention used for the treatment of rust diseases resides in that these are efficient not only for prophylaxis of diseases but for the treatment of already infected plants as well.

The fungicides according to the present invention possess a high efficiency under different agroclimatic conditions including frequent heavy rains where such conventional fungicides as zineb and hydroxycarboxine are low-effective.

One of advantages of the fungicides according to the present invention, aphos in particular, is that they feature a longer period of a fungicidal effect as compared to zineb. This makes it possible to reduce the number of treating cycles. A considerable increase in the yield of winter wheat may be obtained even upon a single prophylactic spring treatment with aphos under the conditions of subsequent intensive development of stalk rust on surrounding plants.

The compounds according to the present invention are not phytotoxical when applied in effective or even substantially higher doses (concentrations). Thus, aphos does not lower the yield of wheat grain or exert a detrimental effect on its quality (sprouting power, viability, etc.) even at 8-times the increase of the dose (concentration).

The compounds according to the present invention also possess a high fungicidal activity in respect to rice piriculariosis (*Piricularia oryzae*), grape mildew (*Plasmopara viticola*), septoriosis or white leaf spot of pear (*Septoria piricola*), apple scab (*Fusicladium dendriticum*), potato late blight (*Phytophthora infestans*). Thus, in the efficiency of of suppressing spores of fungus Piricularia oryzae, aphos is about 40 times as efficient as kitacin currently employed for the treatment of piriculariosis (O,O-diethyl-S-benzylthiophosphate). Unlike kitacin and other organo-phosphorus fungicides employed against rice piriculariosis (kitacin II, inesine, quinosane), O,O-diaryl-1-acyloxy-2,2,2-trichloroethylphosphonates according to the present invention have no foul odor.

The fungicides according to the present invention have low acute or chronical toxicity for warm-blooded animals. Thus, acute toxicity of aphos for white mice upon peroral administration is about 3,500 mg/kg of live weight.

The compounds according to the present invention are rapidly degraded in the biosphere to non-toxic products and become harmless to the environment.

Preparation of compositions according to the present invention is effected by intermixing active ingredients with a suitable carrier. The active principles according to the present invention are employed in conventional preparative forms such as emulsifying concentrates (for a high-volume or small-volume spraying) or in the form of solutions in organic solvents. Concentration of the active principle in preparative forms may be varied within the range of from 10 to 80% by weight.

As the solvents use may be made of alcohols, benzene, xylene, toluene, dimethylsulphoxide, aliphatic hydrocarbons and the like. The solvent should be substantially odorless, non-phytotoxic, inert with respect to the active principle and should not be readily inflammable.

For a better understanding of the present invention, some specific Examples are given hereinbelow, wherefrom Examples 1 and 2 illustrate preparation of the compounds according to the invention and Examples 3 and 15 illustrate fungicidal activity thereof.

EXAMPLE 1

Preparation of O,O-diphenyl-1-acetoxy-2,2,2-trichloroethylphosphonate (1)

Method A

Alternative 1

A mixture of 0.1 mol of phosphorus trichloride, 0.2 mol of phenol, 0.1 mol of chloral hydrate and 20 ml of benzene are heated at reflux until hydrogen chloride liberation from the reaction mass stops (1 to 3 hours) and allowed to stand for 10–12 hours to crystallize. The resulting crystals are separated by filtration, dried to give diphenyl-1-hydroxy-2,2,2-trichlroethylphosphonate, m.p. 116°–119° C., the yield is 89%. After recrystallization from benzene, melting point of the product is 125°–126° C. Found, %: Cl 27.51; P 7.72. $C_{14}H_{12}Cl_3O_4P$. Calculated Cl 27.88; P 8.12.

To a solution of 0.03 mol of diphenyl-1-hydroxy-2,2,2-trichloroethylphosphonate in 15 ml of benzene under stirring and at a temperature of 20°–25° C. there is added 0.06 mol of acetic anhydride containing 1 mol.% of sulphuric acid and the mixture is heated at a temperature within the range of from 65° to 70° C. for a period of from 3 to 4 hours.

The solvent as well as the resulting acetic acid and the excessive amount of acetic anhydride are distilled-off at a temperature within the range of from 100° to 120° C. (10–20 mm Hg) the residue is dissolved in 50 ml of benzene, washed with water and a 2% solution of sodium bicarbonate; the organic layer is dried over magnesium sulphate, the solvent is removed in vacuum and the residue is diphenyl-1-acetoxy-2,2,2-trichloroethylphosphonate in the form of a colorless oil which soon crystallizes. The yield is 81%, melting point 49°–50° C. The compound is distilled at a temperature of from 195° to 198° C. (1–2 mm Hg), $n_D^{20}=1.548$; $d_4^{20}=1.387$. Found, %: C 45.21; H, 3.44; Cl 24.66; P 7.60; $C_{16}H_{14}Cl_3O_5P$. Calculated, %: C 45.26; H 3.34; Cl 25.10; P 7.31.

In the IR-spectrum the following absorption bands are found ($\nu$, $cm^{-1}$): C=0 (1,770); phenyl ring (1,590; 1,480; 950-960; 690); P=0 (1,290); $CCl_3$(840) and there is no absorption band of the OH-group characteristic of the starting diphenyl-1-hydroxy-2,2,2-trichloroethylphosphonate.

PMP-spectrum (in carbon tetrachloride): $\delta_{CH_3}2\pm0.05$ m.d. (singlet); $\delta_{CH}6.15\pm0.05$ m.d. (duplet); $J_{P\text{-}H}12\pm0.2$ Hz; $\delta C_6H_5$ $7.2\pm0.05$ m.d.

Mass-spectrum of the compound has peaks of the molecular ion (M+) m/e 422, 424, 426 (3 chlorine atoms), fragment ions m/e 331, 333, 335 (M—$C_6H_4$—$CH_3$), 287, 289, 291 (M—$C_6H_4$—$CH_3$—$CO_2$) 269, 271 (M—$CH_2COCl$—$CClCHO$, one chlorine atom), 234 (M—$CH_2COCl$—$CCl_2CHO$).

Alternative 2

Into a 1.5 liter three-neck flask there are charged 3 mol of phenol, 1.5 mol of chloral hydrate and 250 ml of anhydrous benzene (or chloroform, carbon tetrachloride, dichloroethane). The thus-produced suspension is added, under stirring for 40–50 minutes, with 1.5 mol of phosphorus trichloride thereupon an intensive reaction occurs accompanied by evolution of hydrogen chloride. After intermixing of the reagents, the reaction mass is heated at reflux under stirring until hydrogen chloride is substantially totally liberated (3–4 hours), whereafter 3 mol of acetic anhydride are added and heating at reflux is continued to complete the reaction (3–4 hours, control by the method of thin-layer chromatography). The solvent as well as the resulting acetic acid and the excessive amount of acetic anhydride are distilled-off at a temperature within the range of from 100° to 120° C. (10–20 mm) to give, as a residue, a crude product with a yield of about 100%.

To purify the resulting product, it is dissolved in 350 ml of chlorobenzene (or chloroform, carbon tetrachloride, dichloroethane), washed with a 2% solution of sodium bicarbonate (twice with portions of 350 ml each) and water (twice with 350 ml portions). The organic layer is separated, the solvent is removed, the residue is set under vacuum of 1–5 mm Hg at a temperature within the range of from 100° to 130° C. to give a product in the form of a colorless oil with $n_D^{20}=1.548$; $d_4^{20}=1{,}390$; $R_f$ 0.64/the system benzene-heptane-acetone in the ratio of 3:3:1); upon storage for 1–2 days the compound is crystallized; melting point is 48°–50° C. The yield is equal to 76–80%. A portion of the compound is completely distilled at a temperature of 197°–198° C./1–2 mm Hg; $n_D^{20}=1.548$; $d_4^{20}=1.390$. Found, %: C 45.68; H 3.41; Cl 24.88; P 7.42.

Alternative 3

In a flask provided with a stirrer and a reflux condenser there are intermixed, at a temperature of from 20° to 40° C., 2 mol of phenol and 1 mol of phosphorus trichloride; temperature of the mixture is gradually increased to 100°–120° C. The reaction mass is cooled to 20°–50° C. and 1 mol of chloral hydrate is portion-wise added thereto. The mixture is heated for a period of from 40 to 80 minutes to a temperature within the range of from 100° to 110° C., whereafter 1.2 mol of acetic anhydride is added thereto and the heating is continued at 90°–110° C. to complete acetylation (1 to 3 hours). The reaction mass is set under vacuum at a temperature of from 80° to 130° C./20-1 mm Hg to give, as a residue, a commercial product in the form of a colorless or slightly colored oil, $n_D^{20}=1.549$–$1.550$ which crystallizes within 1–2 days; melting point is 50°–54° C. The yield is equal to 95–97%.

Alternative 4

Mixture of 0.6 mol of phenol and 0.3 mol of phosphorus trichloride is stirred for 30 minutes at a temperature within the range of from 20° to 30° C., whereafter the mixture temperature is elevated, over a period of one hour, to 110° C.; at this temperature the mixture is stirred for an additional 0.5 hour. The reaction mass is cooled to 20°–30° C. and at this temperature, under stirring, there are simultaneously added 0.3 mol of chloral and 0.3 mol of water. The mixture is heated for 40–50 minutes at a temperature of from 90° to 100° C., whereafter 0.36 mol of acetic anhydride is added thereto and heating is continued at a temperature of from 90° to 110° to complete acetylation (1 to 3 hours). The reaction mass is set under vacuum at a temperature within the range of from 80° to 130° C./20-1 mm Hg to give, as a residue, a product in the form of a colorless oil, $n_D^{20}=1.549$ which crystallizes within 1–2 days, melting point is 50°–52° C. The yield is equal to 93%.

Method B

To a suspension of 0.03 mol of O,O-diphenyl-1-hydroxy-2,2,2-trichloroethylphosphonate and 0.045 mol of acetic acid in 20 ml of chloroform there is added 0.07 mol of chlorosulphonic acid under stirring at a temperature within the range of from 25° to 35° C.; the reaction mixture is agitated for 30 minutes and then, still under stirring, 25 ml of water are gradually added. The organic layer is separated and washed with water (thrice with portions of 25 ml), a 2% solution of sodium bicarbonate (25 ml), again with water and the dried over sodium sulphate; the solvent is removed in vacuum to give, as a residue, a product with $n_D^{20}=1.548$ which crystallizes within 2–3 days, melting point is 49°–52° C.; the yield is equal to 86%.

EXAMPLE 2

Preparation of a mixture of O,O-ditolyl-1-acetoxy-2,2,2-trichloroethylphosphonates A mixture of 0.5 mol of tricresol (crude mixture of ortho-, para- and meta- cresols) and 0.25 mol of phosphorus trichloride is stirred for 0.5 hour at a temperature within the range of from 20° to 30° C., then within one hour the temperature is increased to 110°–120° C.; the reaction mass is maintained under these conditions for an additional 0.5 hour, cooled to a temperature of from 20° to 50° C., added with 0.25 mol of chloral hydrate, heated at a temperature of from 100° to 110° C. till hydrogen chloride evolution stops, then added with 0.3 mol of acetic anhydride and heating is continued to complete acetylation. The reaction mass is set under vacuum at a temperature within the range of from 80° to 130° C./20-1 mm Hg to give, as a residue, in the yield of 100% a mixture of compounds in the form of a slightly-colored oil, $n_D^{20}=1{,}5315$; $d_4^{20}=1.3262$. Found, %: C 47.61; H 4.09; Cl 23.32; P 6.73. $C_{18}H_{18}Cl_3O_5P$. Calculated, %: C 47.86; H 4.02; Cl 23.55; P 6.86.

Under similar conditions other compounds listed in the following Table 1 are prepared.

Table 1

0,0-Diaryl-1-acyloxy-2,2,2-trichloroethylphosphonates

| Compound No. 1 | Formula 2 | Method of preparation 3 | Yield, % 4 | m.p. $n_D^{20}$ °C. 5 | $d_4^{20}$ 6 |
|---|---|---|---|---|---|
| I | 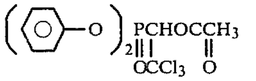 (aphos) | A,B | 76–100 | 1.547–1.549 (48–54) | 1.387–1.398 |
| II | 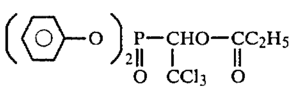 | B | 71.5 | 1.547 (45–46) | — |
| III | 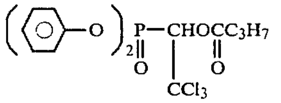 | B | 82 | 1.544 | 1.348 |
| IV | 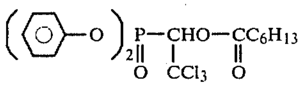 | B | 91 | 1.527 | 1.270 |

Table 1-continued
0,0-Diaryl-1-acyloxy-2,2,2-trichloroethylphosphonates
| Compound No. 1 | Formula 2 | Method of preparation 3 | Yield, % 4 | m.p. $n_D^{20}$ °C. 5 | $d_4^{20}$ 6 |
|---|---|---|---|---|---|
| V | 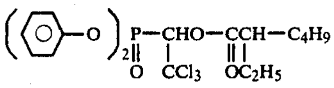 | B | 90.5 | 1.524 | — |
| VI | 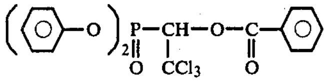 | B | 82.5 | 1.583 (83–85) | |
| VII | 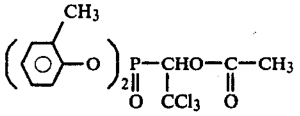 | A-2 | 89 | (56–58) | — |
| VIII | 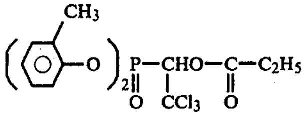 | A-2 | 88 | 1.544 (39) | — |
| IX | 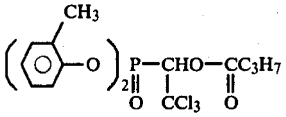 | B | 75 | 1.542 | — |
| X | 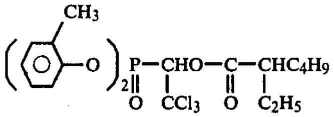 | B | 81 | 1.507 | 1.211 |
| XI | 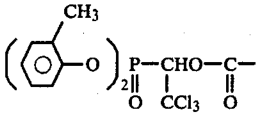 | B | 58 | 1.567 | — |
| XII | 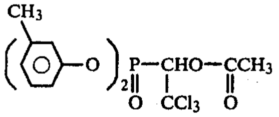 | A-2 | 80 | 1.542 | 1.346 |
| XIII | 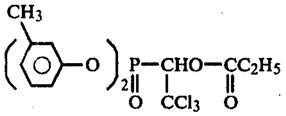 | B | 85,5 | 1.541 | 1.329 |
| XIV | 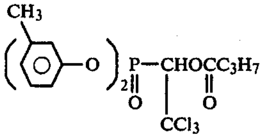 | B | 88 | 1.539 | 1.310 |
| XV | 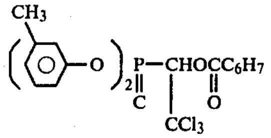 | B | 82 | 1.525 | 1.231 |
| XVI | 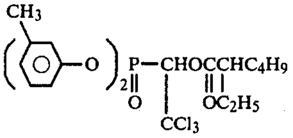 | B | 60 | 1.516 | 1.213 |
| XVII | 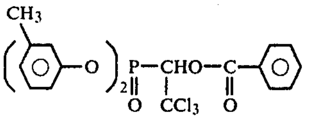 | B | 56 | 1.578 | — |
| XVIII | 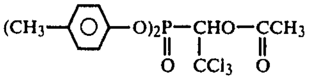 | A-2 | 79 | 1.545 | 1.365 |

Table 1-continued
| 0,0-Diaryl-1-acyloxy-2,2,2-trichloroethylphosphonates | | | | | |
|---|---|---|---|---|---|
| Compound No. 1 | Formula 2 | Method of preparation 3 | Yield, % 4 | m.p. $n_D^{20}$ °C. 5 | $d_4^{20}$ 6 |
| XIX | 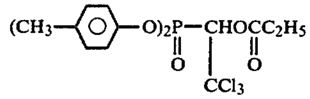 | A-2 | 86 | 1.539 | 1.325 |
| XX | 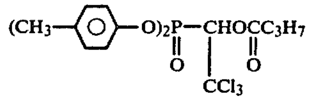 | B | 83 | 1.538 | 1.319 |
| XXI | 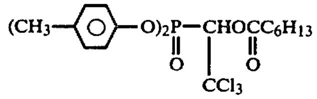 | B | 73 | 1.522 | 1.246 |
| XXII | 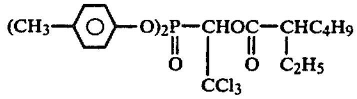 | B | 94 | 1.516 | 1.215 |
| XXIII | 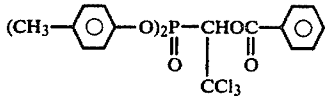 | B | 68 | (94–96) | — |
| XXIV | 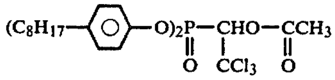 | A-1 | 85 | 1.525 | — |
| XXV | 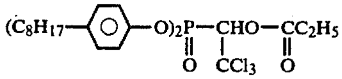 | A-1 | 71 | 1.519 | — |
| XXVI | 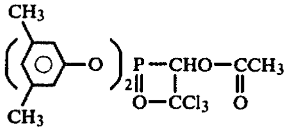 | A-1 | 85 | 1.543 (74–75) | — |
| XXVII | 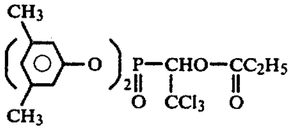 | B | 50 | 1.542 | 1.313 |
| XXVIII | 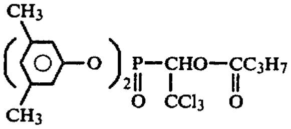 | B | 64 | 1.542 | 1.286 |
| XXIX | 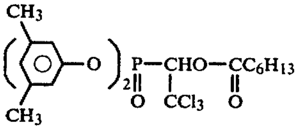 | B | 59 | 1.534 | — |
| XXX | 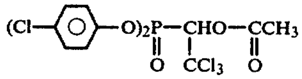 | A-2 | 80 | 1.562 (76–77) | — |
| XXXI | 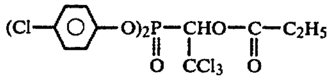 | A-2 | 81,5 | 1.560 (70–71) | — |
| XXXII | 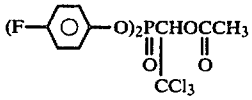 | A-2 | 69 | 1.533 (61–63) | — |
| XXXIII | 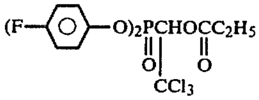 | A-2 | 87 | 1.526 (48–50) | |

Table 1-continued
0,0-Diaryl-1-acyloxy-2,2,2-trichloroethylphosphonates
| Compound No. 1 | Formula 2 | Method of preparation 3 | Yield, % 4 | m.p. $n_D^{20}$ °C. 5 | $d_4^{20}$ 6 |
|---|---|---|---|---|---|
| XXXIV | 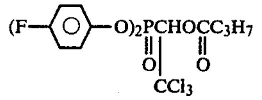 | A-2 | 68.5 | 1.524 (40–42) | — |
| | | B | 72.5 | 1.523 (41–42) | — |
| XXXV | 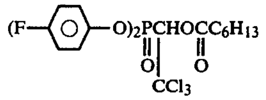 | B | 75.5 | 1.515 | 1.337 |
| XXXVI | 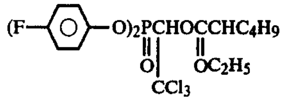 | B | 83 | 1.496 | 1.277 |
| XXXVII | 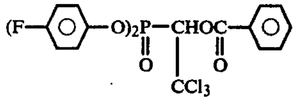 | B | 50 | viscous mass | — |
| XXXVIII | 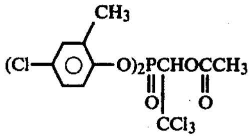 | A-I | 78 | 1.556 | — |
| XXXIX | 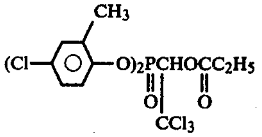 | A-I | 88 | 1.554 | 1.429 |
| XL | 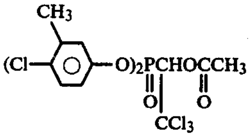 | A-1 | 66 | 1.561 | — |
| XLI | 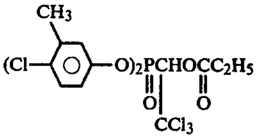 | A-1 | 94.5 | 1.556 | — |
| XLII | 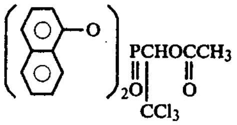 | A-1 | 80 | (96–98) | — |
| XLIII | 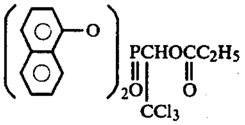 | A-1 | 81 | viscous mass | — |
| XLIV | 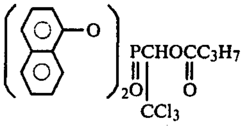 | B | 65 | (68–70) | — |
| XLV | 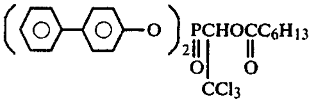 | B | 69 | viscous mass | — |

Table 1-continued 0,0-Diaryl-1-acyloxy-2,2,2-trichloroethylphosphonates

| Compound No. 1 | Formula 2 | Method of preparation 3 | Yield, % 4 | m.p. $n_D^{20}$ °C. 5 | $d_4^{20}$ 6 |
|---|---|---|---|---|---|
| XLVI | 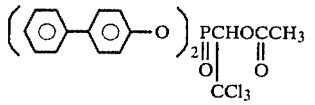 | A-2 | 82.5 | (41-42) | — |
| XLVII | 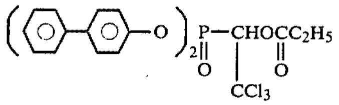 | A-2 | 77 | (56-57) | — |
| XLVIII | 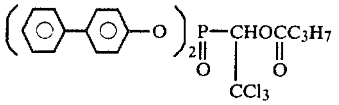 | B | 45 | (65-66) | — |
| XLIX | 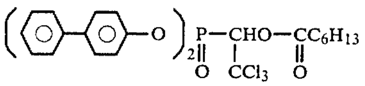 | B | 89 | (88-89) | — |
| L | 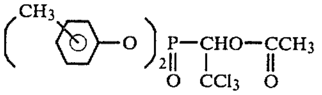 | A-3 | about 100 | 1.532 | — |

EXAMPLE 3

Activity of O,O-diaryl-1-acyloxy-2,2,2-trichloroethylphosphonates against stalk rust of wheat under green-house conditions Wheat plants 10-12 days old are sprayed with emulsions of the compounds being tested three days before the inoculation with uredospores of Puccinia graminis. Working emulsions are prepared by way of mixing the compounds with a surfactant Twin-20 in the ratio of 1:1, dissolution of the mixture in an organic solvent (alcohol, acetone, xylene), followed by dilution of the resulting concentrate with a calculated quantity of water. Activity of the compounds is determined 8-10 days after the inoculation by a lowered number of rust pustules on sprayed plants in comparison with the control. The control plants are sprayed with an emulsion of the surfactant and the solvent in corresponding concentrations. Reproducibility of the experiment: 6 pots with 5 plants in each.

The test results are shown in the following Table 2. As reference fungicides use is made of zineb, chloracetophos. In Table 2 there are also given data illustrating toxicity of the test compounds for warm-blooded animals.

Table 2

Activity of 0,0-diaryl-1-acyloxy-2,2,2-trichloroethylphosphonates against stalk rust of wheat under green-house conditions and their toxicity in respect of warm-blooded animals

| Compound No. according to Table 1 | Pencentage of injury lowered at a concentration, % | | $LD_{50}$ for white mice, mg/kg |
|---|---|---|---|
| 1 | 0.1<br>2 | 0.02<br>3 | 4 |
| I (aphos) | 98-100 | 70-97 | 3,500 |
| II | 78 | 63 | above 1,000 |
| III | 68 | 51 | above 500 |
| IV | 98 | 74 | above |

Table 2-continued

Activity of 0,0-diaryl-1-acyloxy-2,2,2-trichloroethylphosphonates against stalk rust of wheat under green-house conditions and their toxicity in respect of warm-blooded animals

| Compound No. according to Table 1 | Pencentage of injury lowered at a concentration, % | | $LD_{50}$ for white mice, mg/kg |
|---|---|---|---|
| 1 | 0.1<br>2 | 0.02<br>3 | 4 |
| | | | 1,000 |
| V | 74 | 61 | above 1,000 |
| VI | 99 | 98 | above 1,000 |
| VII | 83 | 77 | above 1,000 |
| VIII | 96 | 76 | above 1,000 |
| IX | — | — | above 1,000 |
| X | — | — | above 1,000 |
| XI | — | — | above 1,000 |
| XII | 86 | 68 | above 1,000 |
| XIII | 98 | 85 | above 1,000 |
| XIV | 99 | 92 | above 1,000 |
| XV | 98 | 80 | above 1,000 |
| XVI | 86 | — | above 1,000 |
| XVII | — | — | above 1,000 |
| XVIII | 91 | 63 | above 500 |
| XIX | 100 | 66 | above 1,000 |
| XX | 97 | — | above 1,000 |
| XXI | 97 | — | above 1,000 |
| XXII | 94 | 48 | above 1,000 |
| XXIII | 89 | 79 | above |

Table 2-continued

Activity of 0,0-diaryl-1-acyloxy-2,2,2-trichloroethylphosphonates against stalk rust of wheat under greenhouse conditions and their toxicity in respect of warm-blooded animals

| Compound No. according to Table 1 | Pencentage of injury lowered at a concentration, % 0.1 | 0.02 | $LD_{50}$ for white mice, mg/kg |
|---|---|---|---|
| 1 | 2 | 3 | 4 |
| | | | 1,000 |
| XXIV | 62 | 35 | above 1,000 |
| XXV | 48 | 23 | above 1,000 |
| XXVI | 84 | — | above 1,000 |
| XXVII | 92 | — | above 1,000 |
| XXVIII | 73 | — | above 1,000 |
| XXIX | 85 | — | above 1,000 |
| XXX | 89 | 68 | above 1,000 |
| XXXI | 82 | 59 | above 1,000 |
| XXXII | 100 | 84 | above 1,000 |
| XXXIII | 100 | 62 | above 1,000 |
| XXIV | 99 | 95 | above 1,000 |
| XXXV | — | — | above 1,000 |
| XXXVI | — | — | above 1,000 |
| XXXVII | — | — | above 1,000 |
| XXXVIII | 92 | 53 | above 500 |
| XXXIX | 99,5 | 44 | above 500 |
| XL | 95 | 76 | above 1,000 |
| XLI | 91 | 53 | above 1,000 |
| XLII | 92 | 87 | above 1,000 |
| XLIII | 89 | 72 | above 1,000 |
| XLIV | 71 | — | above 1,000 |
| XLV | 72 | — | above 1,000 |
| XLVI | 97 | 23 | above 1,000 |
| XLVII | 72 | 0 | above 1,000 |
| XLVIII | 67 | — | above 1,000 |
| XLIX | 49 | — | above 1,000 |
| L | 82 | — | — |
| Known: 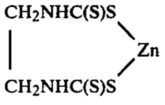 Zineb | 92-99 | 80-97 | 5,200 |
| 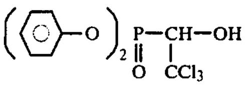 chloracetophos | 71 | 61 | above 400 |
| 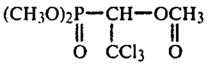 | 54 | 10 | above 1,000 |

EXAMPLE 4

Efficiency of O,O-diaryl-1-acyloxy-2,2,2-trichloroethylphosphonates against stalk rust of wheat under field conditions Efficiency of the compounds was studied in the Moscow region on sowings of spring wheat, Krasnozernaja variety, susceptible to stalk rust (*Puccinia graminis f. tritici*).

The sowing was effected on May 5, sproutings appeared on May 17. Infection background was created by inoculation of the plants in the phase of leaf-tube formation (Stage 6 according to the Feeks scale). The size of experimental plots was 1.5 $m^2$; reproducibility—2 times; plants located in pairs in comparison with the reference and control.

The test compounds were employed in the form of aqueous emulsions prepared from concentrates containing the active principle, solvent and surfactant. The emulsions were applied onto plants by a hydraulic spraying means at a rate of from 700 to 800 l/g. The test compounds and reference fungicide were employed in the dosage of 3 kg/ha as calculated for the active principle. Spraying of the plants with fungicides was effected three times: the first on the day of emergence of uredopustules in inoculated plants, the second and third—after 15 and 12 days respectively.

Injury of plants was evaluated twice: the first time 9 days after the first spraying and for the second time—two weeks after the third spraying. Evaluation was made using the James scale.

Due to unfavorable conditions of the season (heavy rains, shortage of heat and light), the wax-ripeness stage (11.3) occured almost one month later than usually. Harvesting in plots with strongly injured plants was performed as the plants dried-out due to the rust disease.

The test results are shown in Table 3. From Table 3 it is seen that all O,O-diaryl-1-acyloxy-2,2,2-trichloroethylphosphonates according to the present invention possess a fungicidal effect, and the major part thereof are superior over the conventional fungicide zineb as to their degree of the disease suppression and influence on the yield of crops.

Table 3

Efficiency of 0,0-diaryl-1-acylexy-2,2,2-trichloroethylphosphonates against stalk rust of wheat under field conditions

| Compound No according to Table 1 | Percentage of plants injured with rust: 1-st evaluation | 2-nd evaluation | Yield, c/ha | Weight of 1,000 grains, g |
|---|---|---|---|---|
| 1 | 2 | 3 | 4 | 5 |
| I (aphos) | 0.5 | 7.0 | 17.40 | 18.7 |
| II | 0.5 | 11.0 | 11.50 | 16.5 |
| III | 0.5 | 7.0 | 14.00 | 18.4 |
| IV | 0.5 | 6.5 | 20.00 | 23.8 |
| V | 0.5 | 13.0 | 9.50 | 14.8 |
| VI | 0.5 | 8.5 | 11.30 | 16.4 |
| VII | 0.5 | 9.0 | 10.10 | 15.1 |
| VIII | 0.5 | 8.5 | 10.15 | 15.3 |
| XI | 0.5 | 8.0 | 12.40 | 17.8 |
| XII | 0.5 | 8.0 | 11.00 | 16.1 |
| XIII | 0.5 | 10.0 | 12.05 | 16.9 |
| XIV | 0.5 | 7.0 | 12.00 | 17.2 |
| XV | 0.5 | 7.0 | 15.10 | 19.4 |
| XVIII | 0.5 | 6.5 | 17.20 | 21.4 |
| XIX | 0.5 | 8.0 | 14.60 | 18.9 |
| XX | 0.5 | 7.5 | 13.45 | 18.2 |
| XXI | 0.5 | 7.5 | 14.00 | 18.2 |
| XXII | 0.5 | 9.0 | 11.00 | 15.8 |

Table 3-continued

Efficiency of 0,0-diaryl-1-acylexy-2,2,2-trichloroethyl-phosphonates against stalk rust of wheat under field conditions

| Compound No according to Table 1 | Percentage of plants injured with rust | | Yield, c/ha | Weight of 1,000 grains, g |
|---|---|---|---|---|
| | 1-st evaluation | 2-nd evaluation | | |
| 1 | 2 | 3 | 4 | 5 |
| XXIII | 0.5 | 8.0 | 13.30 | 18.1 |
| XXIV | 0.5 | 12.0 | 8.00 | 13.5 |
| XXV | 0.5 | 10.0 | 11.10 | 16.0 |
| XXVI | 0.5 | 10.0 | 11.70 | 16.7 |
| XXVII | 0.5 | 10.5 | 11.50 | 17.1 |
| XXVIII | 0.5 | 7.0 | 11.60 | 16.6 |
| XXIX | 0.5 | 9.5 | 9.75 | 14.8 |
| XXX | 0.5 | 7.0 | 16.70 | 20.9 |
| XXXI | 0.5 | 8.0 | 13.30 | 18.0 |
| XXXIV | 0.5 | 7.4 | 15.10 | 19.6 |
| Zineb (conventional) | 0.5 | 12.0 | 8.55 | 14.0 |
| Control (without spraying) | 0.5 | 15.3 | 7.50 | 13.0 |

EXAMPLE 5

Efficiency of the preparation of Aphos KE (50% emulsion concentrate) against wheat rust under field conditions

| Composition of the preparation is the following, percent by weight: | |
|---|---|
| Active ingredient | 50 |
| Solvent (xylene) | 46 |
| Surfactant (oxyphos) | 4 |

Aphos KE is a transparent light-yellow liquid with a density of 1.07 at the temperature of 20° C., viscosity of 3.6 centipoises at 20° C.

Physical properties of the compound are given in Table 4 below.

Table 4

Physical parameters of the preparation Aphos KE (50% emulsion concentrate)

| Temperature, °C. | Density, g/cm$^3$ | Viscosity, cPs |
|---|---|---|
| 1.5 | 1.0899 | 6.34 |
| 5 | 1.0872 | 5.47 |
| 10 | 1.0826 | 4.67 |
| 15 | 1.0778 | 4.09 |
| 20 | 1.0730 | 3.60 |

Tests of the preparation Aphos KE were conducted under different agroclimatic conditions on sowings of spring and winter wheat susceptible to stalk (*Puccinia graminis f. tritici*) or yellow rust (*P. striiformis*) against an artificial infection background. Tests of brown rust (*P. triticina*) were performed against a natural infection background.

The infection background in the sowings was produced by inoculation thereof with rust uredospores in the stage of tillering-leaf tube formation of the plants (phase 5–6). Original infection was 10 pustules and more per each plant.

Test plots were of 5 or 25 m$^2$; reproducibility of 6 or 5 times respectively; location of similar plots was randomized.

The preparation Aphos KE was used as an aqueous emulsion by spraying the plants with a hydraulic sprayer.

The rate of application of the working liquid was 600 l per one ha. The first spraying was effected on the day of appearance of first uredospores on inoculated plants, the second and the third—with intervals of from 7 to 10 days.

As reference compounds use was made of zineb wettable powder (80%) and hydroxycarboxine wettable powder (75%) with the same application rates.

Efficiency of fungicides is determined by the degree of injury of the plants by rust and also by the grain yield.

The results obtained show that the preparation Aphos KE is a more effective agent for suppression of rust on sowings of grain crops as compared to conventional fungicides hydroxycarboxine and zineb. The test results are given in Tables 5 and 6.

Table 5

Efficiency of the preparation Aphos KE against wheat rust under field conditions

| Test alternatives | Dose, kg/ha of the active principle | Plant injury, % | Yield, c/ha | Weight of 1,000 grains, g |
|---|---|---|---|---|
| 1 | 2 | 3 | 4 | 5 |
| Stalk rust | | | | |
| Moscow region, Spring wheat, Krasnozernaja variety | | | | |
| Aphos KE (3 sprayings) | 3.0 | 7.1 | 16.4 | 17.6 |
| Aphos KE (3 sprayings) | 1.5 | 12.0 | 14.0 | 15.5 |
| Zineb w.p.* (3 sprayings) | 3.0 | 21.0 | 9.2 | 11.7 |
| Zineb w.p. (3 sprayings) | 1.5 | 22.0 | 8.5 | 10.9 |
| Hydroxycarboxine (3 sprayings) | 3.0 | 16.1 | 9.5 | 12.4 |
| Hydroxycarboxine (3 sprayings) | 1.5 | 21.7 | 9.3 | 12.0 |
| Control (no spraying) | — | 22.5 | 8.6 | 10.8 |
| Krasnodar district. Winter wheat, Odesskaja 51 variety | | | | |
| Aphos KE (3 sprayings) | 3.0 | 14.0 | 38.6 | 39.9 |
| Zineb w.p. (3 sprayings) | 3.2 | 16.0 | 34.5 | 35.6 |
| Control (no spraying) | — | 83.0 | 14.0 | 21.0 |
| Yellow rust | | | | |
| Tashkent region, Spring wheat, Kzyl Shark variety | | | | |
| Aphos KE (3 sprayings) | 3.0 | 10.4 | 20.6 | 31.7 |
| Zineb w.p. (3 sprayings) | 3.0 | 14.4 | 20.8 | 31.6 |
| Control (no spraying) | — | 72.7 | 16.5 | 29.7 |

*Wettable powder

Table 6

Efficiency of the preparations Aphos KE and Aphos USVS against wheat rust under field conditions

| Test alternatives | Application rate: kg/ha of active principle | Application rate: of working liquid, l/ha | Rust-injured plants % | Yield, c/ha | Weight of 1,000 grains, g |
|---|---|---|---|---|---|
| 1 | 2 | 3 | 4 | 5 | 6 |
| Stalk rust | | | | | |
| Moscow region, | | | | | |
| Spring wheat Krasnozernaja, | | | | | |
| Triple spraying with an interval of 11–14 days between sprayings | | | | | |
| Infection background - strong, artificial | | | | | |
| Aphos KE (50%) | 3.0 | 600 | 9.0 | 23.4 | 24.7 |
| Zineb, w.p., 80% | 3.0 | 600 | 21.0 | 9.1 | 14.5 |
| Control (no spraying) | — | — | 30.0 | 1.3 | 11.0 |
| Minimal true difference | | | | | |
| at R = 0.05 | | | | 3.2 | 1.7 |
| Krasnodar region, | | | | | |
| Winter wheat Odesskaja 51, | | | | | |
| Triple spraying with an interval between sprayings of 7–8 days | | | | | |
| Infection background - artificial, strong | | | | | |
| Aphos (40%), for USVS | 3.0 | 7.5 | 13.0 | 26.1 | 34.1 |
| Aphos KE (50%) | 3.0 | 600 | 12.0 | 27.9 | 35.5 |
| Zineb w.p., 80% | 3.0 | 600 | 28.0 | 23.7 | 29.7 |
| Control (no spraying) | — | — | 74.0 | 12.6 | 21.2 |
| Minimal true difference | | | | | |
| at R = 0.05 | | | | 5.0 | 4.1 |
| Yellow rust | | | | | |
| Tashkent region, | | | | | |
| Winter wheat Kzyl-Shark, | | | | | |
| Triple spraying with an interval of 7–9 days between sprayings | | | | | |
| Infection background - artificial, strong | | | | | |
| Aphos KE (50%) | 3.0 | 600 | 20.2 | 23.6 | 36.1 |
| Zineb w.p. (80%) | 3.0 | 600 | 19.4 | 24.8 | 35.7 |
| Control (no spraying) | | | 62.7 | 19.7 | 32.2 |
| Minimal true difference | | | | | |
| at R = 0.05 | | | | 3.2 | 1.8 |
| Aphos (40%) for USVS | 3.0 | 7.5 | 34.7 | 19.9 | 33.8 |
| Zineb, w.p. (80%) | 3.0 | 600 | 19.4 | 20.9 | 35.7 |
| Control (no spraying) | — | — | 55.2 | 16.6 | 32.5 |
| Minimal true difference | | | | | |
| at R = 0.05 | | | | 2.7 | 2.3 |
| Brown rust | | | | | |
| Kaliningrad region, | | | | | |
| Winter wheat Mironovskaja 808 | | | | | |
| Single spraying | | | | | |
| Infection background - natural, later development | | | | | |
| Aphos KE (50%) | 3.0 | 600 | 10.2 | 76.0 | 55.1 |
| Zineb 80%, w.p. | 3.0 | 600 | 9.0 | 70.0 | 55.5 |
| Control (no spraying) | — | — | 45.8 | 62.0 | 54.2 |
| Minimal true difference | | | | | |
| at R = 0.05 | | | | 0.7 | 1.2 |

EXAMPLE 6

Efficiency of the preparation Aphos (40%) for USVS against wheat rust underfield conditions

| | |
|---|---|
| 0,0-diphenyl-1-acetoxy-2,2,2-trichloroethylphosphonate-(active principle) | 40 |
| diluent-solvent | 57 |
| auxiliary substance - goudron | 3. |

The preparation comprises a uniform dark-brown liquid with a slight specific odor. Physical parameters of the preparation are given in Table 7 hereinbelow.

Table 7

Physical parameters of the preparation Aphos (40%) for USVS

| Temperature, °C. | Density, $g/cm^3$ | Viscosity, cPs |
|---|---|---|
| 1.5 | 1.0669 | 8.75 |
| 5 | 1.0629 | 7.80 |
| 10 | 1.0587 | 6.92 |
| 15 | 1.0538 | 4.93 |
| 20 | 1.0490 | 4.34 |

Tests of the preparation Aphos for USVS were performed in difference agroclimatic zones on sowings of spring and winter wheat susceptible to stalk (*Puccinia graminis f. tritici*) or yellow (*P. striiformis*) rust by the method of ultra-small volume spraying (USVS).

Infection background in sowings was produced by inoculation thereof with rust uredospores. The initial infection level was 10 and more pustules per one plant.

The size of test plots was 50 or 100 $m^2$; test reproducibility—3 and 5 times respectively; location of plots was random.

The preparation Aphos for USVS was applied onto the plants by means of a disc-fan sprayer Turbair TOT-2S. The application rate of the preparation was 7.5 l/ha. The first spraying was effected on the day of appearance of first uredospores on inoculated plants, the second and the third—in intervals of 7 and 10 days.

As the reference fungicide use was made of zineb (80% wettable powder) which was applied onto the plants in the form of an aqueous suspension by means of a hydraulic sprayer at the rate of application of the working liquid of 600 l/ha.

Efficiency of fungicides is determined by the degree of injury of plants with rust and by the grain yields. The test results are shown in Table 8 hereinbelow.

The results obtained show that the preparation Aphos applied onto plants by the method of ultra-small volume spraying (USVS) is a highly effective composition for suppressing stalk and yellow rust on wheat sowings. Upon a triple application at the rate of 7.5 l/ha the preparation aphos as applied by the USVS method revealed a substantially higher suppression effect on rust than zineb and ensured a much smaller amount of the yield losses.

Table 8

Efficiency of the preparation Aphos for USVS against wheat under field conditions

| Test Alternatives | Dose per 1 ha: kg of active principle | Dose per 1 ha: litres of working liquid | Percentage of injured plants | Grain yield, c/ha | Weight of 1,000 grains, g |
|---|---|---|---|---|---|
| 1 | 2 | 3 | 4 | 5 | 6 |
| Stalk rust | | | | | |
| Moscow region; Spring wheat Krasnozernaja variety | | | | | |
| Aphos-USVS (3 sprayings) | 3.0 | 7.5 | 8.4 | 17.8 | 23.3 |
| Zineb (3 sprayings) | 3.0 | 600 | 23.3 | 8.0 | 12.6 |
| Control (no spraying) | — | — | 27.5 | 6.2 | 10.2 |
| Control (non-infected) | | | 2.0 | 24.6 | 29.1 |
| Krasnodar region, Winter wheat, Odesskaja-51 variety | | | | | |
| Aphos-USVS (3 sprayings) | 3.0 | 7.5 | 18.0 | 38.1 | 39.4 |
| Zineb (3 sprayings) | 3.2 | 600 | 16.0 | 34.5 | 35.6 |
| Control (no spraying) | — | — | 83.0 | 14.0 | 21.0 |
| Control (non-infected) | | | 0 | 45.6 | — |
| Yellow rust | | | | | |
| Taskent region. Spring wheat, Kzyl Shark variety | | | | | |
| Aphos-USVS (3 sprayings) | 3.0 | 7.5 | 13.2 | 22.4 | 32.9 |
| Zineb (3 sprayings) | 3.0 | 600 | 14.4 | 20.8 | 31.6 |
| Control (no spraying) | — | — | 72.7 | 16.5 | 29.7 |
| Control (non-infected) | | | — | 22.5 | 33.2 |

EXAMPLE 7

Comparative efficiency of the preparations Aphos-KE and Zineb against yellow rust of wheat with different intervals between sprayings (Krasnodar region, 1977)

Plants in the leaf-tube formation stage (phase 7 according to the Feekes scale) were infected with anabiosis uredospores of yellow rust (10 mg/m$^2$). Test plots (2 m$^2$) were sprayed with emulsions of Aphos KE and suspensions of Zineb at the rate of application for each spraying of 3 kg/ha as calculated for the active ingredient and rate of application of the working liquid of 600 l/ha. The test results are shown in Table 9 hereinbelow.

Table 9

Comparative efficiency of the preparations Aphos-KE and Zineb against yellow rust of wheat under field conditions with different intervals between sprayings

| Preparation | Date spraying | Percentage of injured plants: 17.05 | Percentage of injured plants: 26.05 | Percentage of injured plants: 2.06 | Yield, g/m$^2$ | Weight of 1,000 grains, g |
|---|---|---|---|---|---|---|
| 1 | 2 | 3 | 4 | 5 | 6 | 7 |
| 1. APHOS | 29.04<br>7.05<br>16.05 | 4 | 9 | 21 | 410 | 35.0 |
| 2. ZINEB | " | 4 | 14 | 30 | 411 | 35.4 |
| 3. APHOS | 29.04<br>16.05<br>23.05 | 4 | 16 | 46 | 399 | 33.6 |
| 4. ZINEB | 29.04<br>16.05<br>23.05 | 6 | 44 | 89 | 351 | 31.0 |
| 5. ZINEB | 29.04<br>7.05<br>16.05<br>23.05 | 5 | 9 | 33 | 412 | 34.8 |
| 6. Control (non-protected) | — | 6 | 67 | 91 | 320 | 30.2 |
| Minimal true difference at R = 0.05 | | | | | 32 | 1.9 |

The results obtained show that with longer intervals between sprayings and the same number of treatments (alternatives 3 and 4), efficiency of Aphos is rather high, whereas efficiency of Zineb is substantially reduced to zero. Yield from the plots treated with Aphos was truly higher as compared to the yield from the plots treated with Zineb.

EXAMPLE 8

Efficiency of the preparation Aphos KE against stalk rust of winter wheat at a single spring prophylactic treatment (Moscow region, 1977)

The plants in the stage of leaf-tube formation (phase 8 according to the Feekes scale) were sprayed with Aphos in the dose of 3 kg/ha as calculated for the active ingredient at the rate of application of the working liquid of 600 l/ha. At this time no stalk rust was observed in test plots, whereas on the surrounding sowings the degree of injury was about 1 pustule per stem (0.1%). After some time the stalk rust from the surrounding sowings was spread over the test plots; however, the degree of injury of the protected plants was substantially lower as compared to that for the non-protected plants. Weight of 1,000 grains from the protected plots was 29.7 g, that for the non-protected plots was 24.0 g.

EXAMPLE 9

Influence of Aphos in various doses on wheat plants and yield of crops (evaluation of phytotoxicity)

In tests of the preparation Aphos KE for fungicidal activity no signs of phytotoxicity were observed.

In order to evaluate the effect of the preparation on productivity of the plants and quality of the harvest, the non-infected sowings of spring wheat were thrice sprayed with an aqueous emulsion of Aphos KE in doses of 3, 6, 12 and 24 kg/ha as calculated for the active principle.

The size of test plots was 3 $m^2$; the tests were reproduced for 6 times; similar plots were located at random (Latin square). The first spraying was performed at the moment of leaf-tube formation, the second and third—with intervals of 10 days. As a control, a test alternative was made where the plots were sprayed with zineb at the dose of 3 kg/ha based on the active principle after every 5 days.

In evaluation of phytocidal properties use was made of the 5-point scale (0—no phytotoxicity; 4—complete death of the plants). The test results are shown in the following Table 10.

Table 10

Effect of Aphos in different doses on wheat plants and yield of crops (Moscow region)

| Test alternative | Dose, kg/ha of a.p.* | Yield, c/ha | Weight of 1,000 grains, g | Phytocidal effect, points |
|---|---|---|---|---|
| Aphos KE (3 sprayings) | 3.0 | 27.1 | 33.9 | 0 |
| Aphos KE (3 sprayings) | 6.0 | 28.8 | 35.6 | 0 |
| Aphos KE (3 sprayings) | 12.0 | 20.3 | 36.1 | 0 |
| Aphos KE (3 sprayings) | 24.0 | 29.9 | 37.5 | 1,5 |
| Zineb w.p.** (8 sprayings) | 3.0 | 24.6 | 29.1 | 0 |

*active principle
**wettable powder

It is seen from Table 10 that Aphos KE caused lesions of leaves only when applied in the dose of 24 kg/ha without, however, exerting a detrimental effect on the yield of crops and grain quality.

The use of aphos during the period of plant vegetation provided no detrimental effect on sowing qualities of seeds either. After storage of grains for one year the sprouting energy and germination power were 98.5 and 99.5% respectively.

EXAMPLE 10

Efficiency of the preparation Aphos KE against grape mildew (*Plasmopara viticola*)

The tests were performed under the conditions of humid subtropics (Adzharskaja ASSR). Spraying for 6 times was effected within time limits determined from the Müller scale. As the reference compound use was made of Zineb (80% wettable powder).

Percentage of the disease progress was calculated according to the formula:

$$R=\Sigma fp\cdot 100/n\cdot C$$

wherein $\Sigma_{fp}$—sum of frequency of points;

n—number of evaluated leaves and fruits

C—maximal point of the scale used.

The test results are given in Table 11 hereinbelow.

Table 11

Efficiency of Aphos against grape mildew

| Test alternatives | Preparation concentration, % | Percentage of disease development | Percentage of disease suppressed |
|---|---|---|---|
| Aphos-KE (50%) | 0.2 | 8.9 | 87.0 |
| Aphos-KE (50%) | 0.5 | 2.3 | 96.5 |
| Zineb w.p. (80%) | 0.4 | 1.8 | 98.3 |
| Control (no spraying) | — | 65.5 | — |

EXAMPLE 11

Efficiency of the preparation Aphos KE against Septoria leaf spot of pear (*Septoria piricola*)

The tests were performed under humid subtropical conditions (Adzharskaja ASSR). Spraying was effected for 3 times with intervals of 15–16 days. As the reference preparation use was made of zineb.

Percentage of the disease suppression was evaluated by the formula:

$$X=(K-b)\cdot 100/K$$

wherein

K—degree of injury of the control plants;

b—injury of plants in the test alternative.

Test results are shown in the following Table 12.

Table 12

Efficiency of Aphos-KE against Septoria leaf spot of pear

| Test alternative | Preparation concentration, % | Number of spots per one leaf | Percentage of disease suppressed |
|---|---|---|---|
| Aphos-KE (50%) | 0.2 | 3.2 | 81.0 |
| Aphos-KE (50%) | 0.5 | 2.3 | 89.0 |
| Zineb w.p. (80%) | 0.4 | 2.9 | 85.0 |
| Control (no spraying) | — | 15.3 | — |

EXAMPLE 12

Efficiency of the preparation Aphos-KE against apple scab Krasnodar region

The tests were performed with branches cut from an apple tree of the Simirenko renet variety susceptible to apple scab. The branches with young leaves in the age of 8–12 days were placed in vessels with the Knop solution and kept therein till the end of experiments.

The treatment was effected using a 0.1% emulsion of Aphos; attention was paid to a uniform distribution of the emulsion over the upper and lower surfaces of leaves. One day after the treatment with the fungicide, the apple branches were sprayed with an aqueous spore suspension of the fungus *Venturia inaequalis* (50,000 spores in 1 ml of the suspension). Use was made of the fungi conidia collected in the garden from the injured apple leaves.

The infected plants were placed into humid chambers and maintained at a temperature of 20° C. for 24 hours. On expiration of this period the plants were withdrawn from the humid chamber and allowed to stay in the same premises at the same temperature. Relative humidity in the premises was below 76%. First signs of scab were noticed after 8–10 days of residence under these conditions.

Evaluation of injury with scab was effected using a 6-point scale. Injury of four upper leaves was taken into consideration. Test reproduction—3 branches.

Under the above-mentioned conditions aphos ensured complete protection of the apple tree from scab, whereas zineb reduced the degree of injury by 97% as compared to the control.

EXAMPLE 13

Toxicity of Aphos for spores *Piricularia oryzae* Cav.

Spores of the fungus *P. oryzae* were placed for growing in a drop of an aqueo-acetone solution of aphos in the presence of an emulsifying agent Twin-80 in concentrations progressively diminishing from 50 to 0.05 mg/l. 24 hours later the number of sprouted and non-sprouted spores was evaluated using a microscope. In each test alternative 300 spores were taken into account; test reproduction—3 times. The concentration of aphos resulting in a 50% death of spores was determined.

As the reference compound use was made of kitacin in the same concentrations; as the non-protected control use was made of an aqueo-acetone emulsion of Twin-80 in the maximal of the test concentrations. As shown by the results obtained, aphos is superior over kitacin by about 50 times in respect of activity.

The test results are given in the following Table 13.

Table 13

Toxicity of Aphos for spores of *P.oryzae* fungus

| Test alternative | Concentration causing 50% death of spores, mg/l |
|---|---|
| Treatment with Aphos | 0.69 |
| Treatment with kitacin | 28.6 |
| In the control 98–99% of spores were sprouted. | |

EXAMPLE 14

Efficiency of the preparation Aphos-KE against potato phytophthora (*Phytophthora infestans*)

The tests were performed by way of treatment of the tubers injured with phytophthora. The tubers were treated with a 1% aqueous emulsion of the preparation to ensure total wetting thereof, kept in a humid chamber at the temperature of 18° C. for 14 days, whereafter sporulation intensity was determined.

As the reference compound use was made of tetramethylthiuramdisulphide (TMTD) in the same concentration. As the control use was made of similar tubers non-treated with the fungicide.

The tests showed that no sporulation was observed on the tubers treated with the preparation Aphos. In the test alternative with TMTD individual conidia were observed, whereas in the control, sporulation was very intensive.

EXAMPLE 15

Toxicity of O.O-diaryl-1-acyloxy-2,2,2-trichloroethylphosphonates in respect of warm-blooded animals Toxicity ($LD_{50}$) was evaluated on males and females of white mice with peroral administration of the compounds. A portion of the test compound was mixed with the emulsifier Twin-20 and diluted with distilled water to the required working concentration. Administration of the preparation was effected by means of a metal probe and syringe directly into the stomach of test animals 2–3 hours after feeding. The tests were performed using several doses, 6 animals per each dose. Subsequent observation was effected for two weeks.

The test results are shown in Tables 2 and 14.

Table 14

Toxicity of the active principle 0.0-diphenyl-1-actoxy-2,2,2-trichloroethylphosphonate and preparations based thereon in respect of warm-blooded animals

| Compound and preparations | Animals | $LD_{50}$ with trusty limits, mg/kg | $LD_{90}$ with trusty limits, mg/kg |
|---|---|---|---|
| 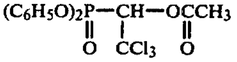 | mice ♀ | 3,500 (2,710–4,521) | 8,200 (5,098–13,146) |
| Aphos-KE (50%) | mice ♀ | 3,600 (3,009–4,361) | 5,900 (4,604–7,556) |
| Aphos-USVS(40%) | mice ♂ | (2,034–2,749) | 3,300 (2,246–4,184) |
| | mice ♀ | (2.243–3,571) | 4,700 (3,615–6,105) |

What is claimed is:

1. O,O-diaryl-1-acyloxy-2,2,2-trichloroethylphosphonates of the formula:

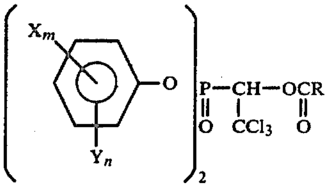

wherein

R is a $C_1$-$C_8$-alkyl, phenyl;

X and Y the same or different are each hydrogen, a $C_1$-$C_8$-alkyl, phenyl, a halide, or X and Y together form a fragment of a benzene ring;

m and n=1 to 2.

2. A fungicidal composition containing, as the active principle, O,O-diaryl-1-acyloxy-2,2,2-trichloroethylphosphonate of the formula:

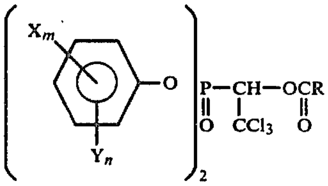

wherein

R is a $C_1$-$C_8$-alkyl, phenyl;

X and Y the same or different are each hydrogen, a $C_1$-$C_8$-alkyl, phenyl, a halide, or X and Y together form a fragment of a benzene ring; m and n=1 to 2, and a carrier therefor.

3. A fungicidal composition as claimed in claim 2, wherein the active principle is contained in an amount of from 10 to 80% by weight.

4. A fungicidal composition as claimed in claim 2, wherein the active principle is O,O-diphenyl-1-acetoxy-2,2,2-trichloroethylphosphonate.

5. A method of suppressing fungal diseases of plants involving the use of a fungicidally active amount of a composition containing, as the active principle, a O,O- diaryl-1-acyloxy-2,2,2-trichloroethylphosphonate of the formula:

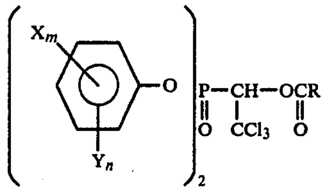

wherein R is a $C_1$-$C_8$ alkyl, phenyl; X and Y the same or different are each hydrogen, a $C_1$-$C_8$ alkyl, phenyl, a halogen, or X and Y together form a fragment of a benzene ring; m and n=1-2, and a carrier therefor.

6. A method as claimed in claim 5, wherein the composition contains the active principle in an amount ranging from 10 to 80% by weight.

7. A method as claimed in claim 5, wherein the active principle is O,O-diphenyl-1-acetoxy-2,2,2-trichloroethylphosphonate.

* * * * *